United States Patent
Harding et al.

(10) Patent No.: US 10,641,725 B2
(45) Date of Patent: *May 5, 2020

(54) ANALYTE DETERMINATION METHOD AND ANALYTE METER

(71) Applicant: AgaMatrix, Inc., Salem, NH (US)

(72) Inventors: Ian Harding, Wells (GB); Richard Williams, Somerville, MA (US); Sridhar Iyengar, Salem, NH (US)

(73) Assignee: AgaMatrix, Inc., Salem, NH (US)

( * ) Notice: Subject to any disclaimer, the term of this patent is extended or adjusted under 35 U.S.C. 154(b) by 226 days.

This patent is subject to a terminal disclaimer.

(21) Appl. No.: 15/825,598

(22) Filed: Nov. 29, 2017

(65) Prior Publication Data

US 2018/0080895 A1    Mar. 22, 2018

Related U.S. Application Data

(60) Continuation of application No. 14/987,895, filed on Jan. 5, 2016, now Pat. No. 9,857,324, which is a continuation of application No. 14/278,299, filed on May 15, 2014, now Pat. No. 9,234,862, which is a continuation of application No. 13/723,713, filed on Dec. 21, 2012, now Pat. No. 8,758,594, which is a continuation of application No. 13/191,831, filed on
(Continued)

(51) Int. Cl.
*G01N 27/327* (2006.01)
*C12Q 1/00* (2006.01)
*G01N 27/30* (2006.01)

(52) U.S. Cl.
CPC ......... *G01N 27/3274* (2013.01); *C12Q 1/006* (2013.01); *G01N 27/307* (2013.01); *G01N 27/327* (2013.01); *G01N 27/3272* (2013.01); *G01N 27/3273* (2013.01)

(58) Field of Classification Search
CPC .......................................... G01N 27/327–3274
See application file for complete search history.

(56) References Cited

U.S. PATENT DOCUMENTS

| | | |
|---|---|---|
| 5,243,516 A | 9/1993 | White |
| 5,266,179 A | 11/1993 | Nankai et al. |
| (Continued) | | |

FOREIGN PATENT DOCUMENTS

| | | |
|---|---|---|
| EP | 1369684 A | 12/2003 |
| JP | H11-230934 A1 | 8/1999 |
| (Continued) | | |

OTHER PUBLICATIONS

Entry for term "multiply", online version of Webster's Third International Dictionary, Unabridged; Copyright 1993.
(Continued)

*Primary Examiner* — J. Christopher Ball
(74) *Attorney, Agent, or Firm* — Larson & Anderson, LLC

(57) ABSTRACT

The presence of oxygen or red blood cells in a sample applied to an electrochemical test strip that makes use of a reduced mediator is corrected for by an additive correction factor that is determined as a function of the temperature of the sample and a measurement that reflects the oxygen carrying capacity of the sample. The measured oxygen carrying capacity can also be used to determine hematocrit and to distinguish between blood samples and control solutions applied to a test strip.

14 Claims, 11 Drawing Sheets

Related U.S. Application Data

Jul. 27, 2011, now Pat. No. 8,361,307, which is a continuation of application No. 13/106,361, filed on May 12, 2011, now Pat. No. 8,329,025, which is a division of application No. 10/907,803, filed on Apr. 15, 2005, now Pat. No. 7,964,089.

(56) References Cited

U.S. PATENT DOCUMENTS

| | | | |
|---|---|---|---|
| 5,320,732 | A | 6/1994 | Nankai et al. |
| 5,352,351 | A | 10/1994 | White et al. |
| 5,438,271 | A | 8/1995 | White et al. |
| 5,942,102 | A | 8/1999 | Hodges et al. |
| 5,989,917 | A | 11/1999 | McAleer et al. |
| 6,241,862 | B1 | 6/2001 | McAleer et al. |
| 6,251,260 | B1 | 6/2001 | Heller et al. |
| 6,284,125 | B1 | 9/2001 | Hodges et al. |
| 6,287,451 | B1 | 9/2001 | Winarta et al. |
| 6,391,645 | B1 | 5/2002 | Huang et al. |
| 6,475,372 | B1 | 11/2002 | Ohara et al. |
| 6,592,745 | B1 | 7/2003 | Feldman et al. |
| 6,616,819 | B1 | 9/2003 | Liamos et al. |
| 6,645,368 | B1 | 11/2003 | Beaty et al. |
| 7,964,089 | B2 | 6/2011 | Harding et al. |
| 9,857,324 | B2 * | 1/2018 | Harding ............... C12Q 1/006 |
| 2002/0139692 | A1 | 10/2002 | Tokunaga et al. |
| 2003/0064525 | A1 | 4/2003 | Liess |
| 2003/0178322 | A1 | 9/2003 | Iyengar et al. |
| 2004/0157339 | A1 | 8/2004 | Burke et al. |
| 2005/0067301 | A1 | 3/2005 | Morita et al. |
| 2005/0069892 | A1 | 3/2005 | Iyengar et al. |
| 2005/0109637 | A1 | 5/2005 | Iyengar et al. |
| 2005/0265094 | A1 | 12/2005 | Harding et al. |

FOREIGN PATENT DOCUMENTS

| | | |
|---|---|---|
| WO | 9932881 A1 | 7/1999 |
| WO | 03060154 A2 | 7/2003 |
| WO | 03069304 A2 | 8/2003 |
| WO | 2005022143 A2 | 3/2005 |

OTHER PUBLICATIONS

Dock E. et al., Multivariate data analysis of dynamic amperometric biosensor responses from binary analyte mixtures—application of sensitivity correction algorithms, Talanta, 2005, pp. 298-305, vol. 65, No. 2, Publisher: Elsevier, Amsterdam, NL.

Entry for term "hematocrit" downloaded from MedicalDictionaryWeb.com on Apr. 5, 2012 ; URL: http:www.medicaldictionaryweb.com/Hematocrit-definition/.

* cited by examiner

ANALYTE DETERMINATION METHOD AND ANALYTE METER

BACKGROUND OF THE INVENTION

This application relates to a method for correcting for the presence of oxygen in an electrochemical test strip that makes use of a reduced mediator, to a meter and meter-test strip combination that perform the method in analyzing samples, and to a method and apparatus for determination of hematocrit. The invention also provides a method and apparatus for distinguishing between blood samples and control solutions applied to electrochemical test strips.

Small disposable electrochemical test strips are frequently used in the monitoring of blood glucose by diabetics. Such test strips can also be employed in the detection of other physiological chemicals of interest and substances of abuse. In general, the test strip comprises at least two electrodes and appropriate reagents for the test to be performed, and is manufactured as a single use, disposable element. The test strip is combined with a sample such as blood, saliva or urine before or after insertion in a reusable meter, which contains the mechanisms for detecting and processing an electrochemical signal from the test strip into an indication of the presence/absence or quantity of the analyte determined by the test strip.

Electrochemical detection of glucose is conventionally achieved by applying a potential to an electrochemical cell containing a sample to be evaluated for the presence/amount of glucose, an enzyme that oxidizes glucose, such as glucose oxidase, and a redox mediator. As shown in FIG. 1, the enzyme oxidizes glucose to form gluconolactone and a reduced form of the enzyme. Oxidized mediator reacts with the reduced enzyme to regenerate the active oxidase and produce a reduced mediator. Reduced mediator is oxidized at one of the electrodes, and then diffuses back to either be reduced at the other electrode or by the reduced enzyme to complete the cycle, and to result in a measurable current. The measured current is related to the amount of glucose in the sample, and various techniques for determining glucose concentrations in such a system are known. (See, U.S. Pat. Nos. 6,284,125; 5,942,102; 5,352,351; and 5,243,516, which are incorporated herein by reference.)

One source of variability in the measurements achieved with such systems is the amount of oxygen that is present in the sample. (See U.S. Pat. No. 6,251,260) Oxygen can interact with the reduced enzyme to regenerate oxidized enzyme. Since this process results in oxygen consumption and not in the production of reduced mediator, glucose is consumed without generation of the charge carrier. As a result, the apparent glucose reading is low. Oxygen can also be consumed by reaction with reduced mediator to generate oxidized mediator, and this process also results in an artificially low value of glucose.

Because hemoglobin in red blood cells can act as a reservoir of oxygen, it has been proposed to structure electrochemical test strips so as to exclude red blood cells from the area where the enzyme and mediator are located. (See, for example, U.S. Pat. No. 6,241,862)

It has been suggested to make corrections to the glucose reading based on a hematocrit determination on the sample. For example, U.S. Pat. No. 6,475,372 discloses a method in which a sample is introduced into an electrochemical cell having a working and reference electrode. A first electric potential is applied to the cell and the resultant cell current over a first period of time is measured to determine a first time-current transient. A second electric potential of opposite polarity is then applied to the cell and a second time-current transient is determined. The preliminary concentration of the analyte (CO) is then calculated from the first and/or second time-current transients. This preliminary analyte concentration, less a background value, is then multiplied by a hematocrit correction factor to obtain the analyte concentration in the sample, where the hematocrit correction factor is a function of the preliminary analyte concentration and the ratio of 2 current values within the time-current transient of the electrochemical cell. U.S. Pat. No. 6,287,451 discloses a method in which a hematocrit correction is made to analyte concentration, and measure of hematocrit is determined based on a measured resistance between a working electrode and a reference electrode.

Correction for the presence of red blood cells can be based on either or both of two approaches: a mobility-based approach that removes the affects of hematocrit to produce a glucose measure that is independent of the physical aspects of red blood cells, and a chemical approach that accounts for oxygen attrition which is related to the amount of hemoglobin as an oxygen carrier. The first of these approaches is reflected in a difference in slope of the glucose calibration curve as a function of hematocrit, and as such it is corrected by a multiplicative factor. The second approach is reflected in an offset among glucose calibration curves as a function of hematocrit and it is corrected with an additive factor. The present invention relates to corrections based on the second approach, although it can be used in combination with corrections based on the first approach.

SUMMARY OF THE INVENTION

The present invention relates to the electrochemical determination of analyte in systems using a reduced mediator as a charge carrier and provides an additive correction for the presence of oxygen in the sample. In accordance with the invention, a method is provided for determining an analyte in a sample comprising the steps of:

(a) placing the sample in an electrochemical test cell comprising a working and a counter electrode and a mediator that serves as a charge carrier in the electrochemical determination of the analyte, (b) electrochemically determining an uncorrected result for the determination of analyte in the sample;

(c) determining an additive correction factor for the amount of oxygen in the sample, and (d) modifying the uncorrected result of step (b) with the correction factor of step (c) to provide a corrected determination of analyte in the sample, wherein the additive correction factor for the amount of oxygen in the sample is determined as a function of the temperature of the sample and a measurement that reflects the oxygen carrying capacity of the sample.

In an embodiment of the invention, a potential is applied to a sample in an electrochemical test cell, and an electrochemical signal is observed from which a determination of a raw analyte concentration can be made. The potential is then switched off, and the time required for the potential between the electrodes to decay to a pre-defined level, for example 50 mV, is determined. This time, tmob, is indicative of the mobility of mediator in the sample. An additive correction factor is then determined as a function of tmob and the temperature of the sample, and used to correct the raw analyte reading for oxygen in the sample.

In a further aspect of the invention, a meter for determination of an analyte, such as glucose, that applies the additive correction for glucose is provided.

In a further aspect of the invention, a system comprising a meter for determination of an analyte, such as glucose, that applies the additive correction for glucose, and an electrochemical test strip is provided.

In a further aspect, the invention provides a method and apparatus for determination of hematocrit.

In a further aspect, the present invention provides a method and apparatus for distinguishing between a blood sample and a control solution applied to an electrochemical test strip.

BRIEF DESCRIPTION OF THE DRAWINGS

The invention will be described with respect to a drawing in several figures.

DETAILED DESCRIPTION OF THE INVENTION

I. Definitions

Figure 1:
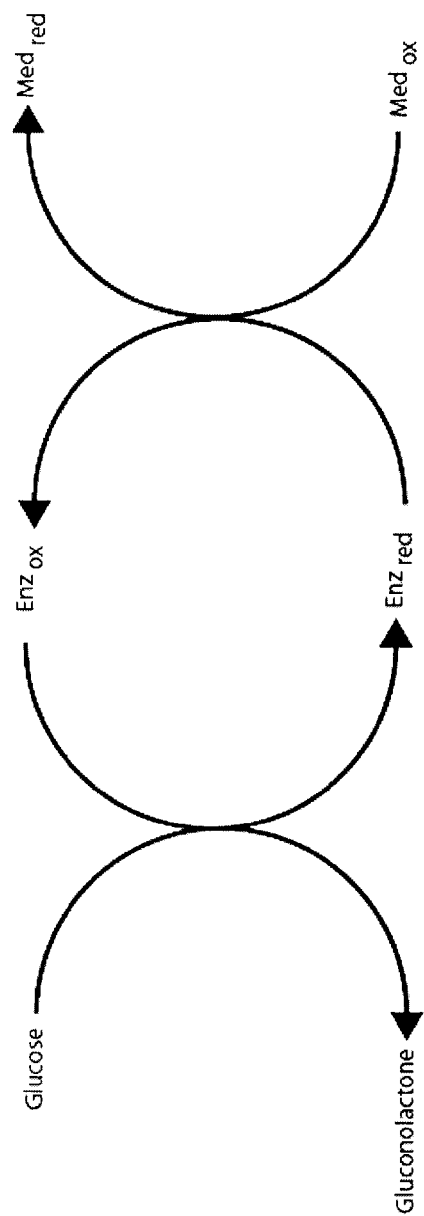
FIG. 1 shows the electron transfer reactions that occur in a conventional amperometric glucose detector.

As used in the specification and claims of this application, the following definitions should be applied:

(a) "additive correction factor" refers to the numerical correction that is added to a raw determination for analyte concentration to arrive at a corrected value. "Additive" encompasses the addition of a negatively signed value, and thus is equivalent to addition or subtraction. Application of this additive correction factor results in an offset of the determined values.

(b) "analyte" refers to a material of interest that may be present in a sample. In the present application, the examples use glucose as an analyte, but the present invention is independent of both the type and amount of analyte. Accordingly, application to glucose detection systems should be viewed as merely a specific and non-limiting embodiment. In some cases, there may be one or more intermediate species between the actual analyte and the mediator. Any such intermediate species are also referred to herein as an analyte.

(c) "determination of an analyte" refers to qualitative, semi-quantitative and quantitative processes for evaluating a sample. In a qualitative evaluation, a result indicates whether or not analyte was detected in the sample. In a semi-quantitative evaluation, the result indicates whether or not analyte is present above some pre-defined threshold. In a quantitative evaluation, the result is a numerical indication of the amount of analyte present. The term "determination of an analyte" may encompass several steps, such that the measured species is related in amount to the analyte, even though it is not related chemically.

(d) "mediator" refers to a chemical species that is electrochemically detected. Numerous electron transfer mediators suitable for detection of analytes such as glucose are known, and include without limitation iron, ruthenium, and osmium compounds. In some embodiments of the invention, the mediator is produced through one or more reaction steps and is related to the concentration of the actual analyte, such as glucose. The present invention is also applicable, however, to circumstances in which the detected chemical species is the reduced form of the analyte to be detected, and this is also an embodiment of the invention.

(e) "mobility" refers to the mobility of the mediator in the electrochemical test cell. Mediator mobility is a property of the mediator itself, i.e., the diffusion coefficient, but is also dependent on other sample properties such as hematocrit and viscosity.

(f) "oxygen attrition" is the discrepancy between measured reduced mediator concentration and actual analyte concentration as a result of the action of oxygen, and is corrected using an additive correction factor.

(g) "oxygen carrying capacity" refers to the capacity of the sample to hold oxygen, in dissolved form and in a red blood cell reservoir.

(h) "predetermined" is used in this application to refer to amounts or values that are determined empirically for a particular meter or test strip or meter/strip combination. The predetermined amounts or values will reflect an optimization for the needs of the user, taking into account the confidence levels needed, and need not achieve the best possible results or 100% accuracy.

(i) "switching off" of the applied potential refers to the creation of an open circuit that forces the current to be zero (by opening a switch or introducing a high impedance into the circuit) that allows a built-up chemical concentration gradient and ion adsorption in the double layer to determine the potential between the electrodes. This is not the same thing as setting the voltage to zero volts.

(j) "$t_{mob}$" is a time determined experimentally during an analysis that reflects the mobility of mediator in a particular sample in a particular test cell. $t_{mob}$ is the time after the applied potential is switched off, that it takes for the potential between the electrodes to decay to a pre-determined value.

II. Oxygen as an Interferent in Electrochemical Reactions

The present invention is directed to solving the problem of sample-dependent errors due to oxygen and to providing a correction for these errors in the measurement of glucose and other oxidizable analytes such as lactate, cholesterol and ethanol in samples where a reduced mediator is produced and serves as a charge carrier. The invention is applicable to samples in which oxygen attrition is a concern, particularly where an oxygen reservoir, or other similar source of residual oxidation capability is present. In particular, the invention is applicable to blood samples that contain red blood cells that act as an oxygen reservoir.

Figure 4A:
FIGS. 4A-D show locations in the reaction pathway where oxygen attrition can occur.

FIGS. 4A-D show a minimal representation of the reaction occurring in an electrochemical cell, and the locations where oxygen attrition can occur. FIG. 4A shows the basic reaction in which analyte is used to generate mediator which is measured to produce a signal. The "chemical change" noted does not imply that the analyte and the mediator are structurally related, but indicates only a chemical process, such as one or more electron transfer reactions, such that mediator is generated as a result of the presence of analyte.

Figure 4B:
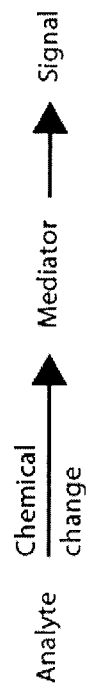
Figure 4C:
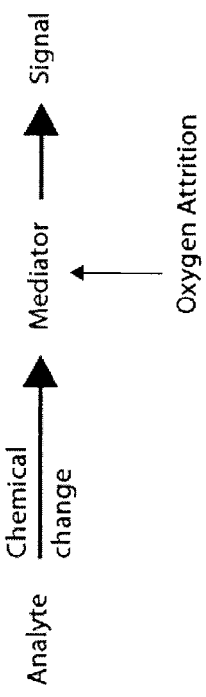
Figure 4D:
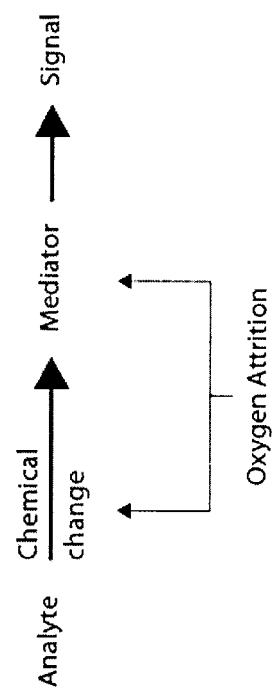

FIG. 4B indicates that oxygen attrition can occur as a result of oxygen interaction with the chemical change, for example oxidation of enzyme. FIG. 4C indicates that oxygen attrition can occur as a result of oxygen interaction with the mediator. Finally, as shown in FIG. 4D, both processes may occur where oxygen availability is high or the rates of the two processes are similar. Any of the processes depicted in FIGS. 4-D introduce error into the assumption that [analyte] ∝[mediator], and results in a reduction in the amount of observed current and a low reading for glucose.

Oxygen is present in blood samples as dissolved oxygen in equilibrium with oxygen bound to hemoglobin. Thus, the hemoglobin in red blood cells acts as reservoir for oxygen, and oxygen-related error may be greater in samples with high hematocrit.

Direct measurement of available oxygen in a blood sample within a low cost disposable test strip is not feasible. Furthermore, the reaction of $O_2$ with reduced mediator does not necessarily proceed to completion, i.e. to consumption of all $O_2$. Thus, merely knowing the amount of $O_2$ may not yield an appropriate correction factor. The reaction is related to the availability of $O_2$ however, and certain aspects of the oxygen availabilty are accessible for measurement, and these are utilized in the present invention. Oxygen availability can be represented generally by the equation:

$O_2$ availability=$f(O_2$ activity, amount of $O_2$)

and may be given by $O_2$ availability=$O_2$ activity×amount of oxygen in an idealized case, where $O_2$ activity is a function of temperature and $pO_2$ and the amount of $O_2$ is a function of the oxygen carrying capacity (OCC) of the sample.

III. Electrochemical Test Cells Useful in the Invention

The present invention is applicable to electrochemical test cells, including disposable test strips with the following characteristics:

(1) at least two electrodes, a working and counter electrodes; and (2) an enzyme that oxidizes the analyte and a redox mediator that oxidizes the reduced enzyme.

In addition to the characteristics listed above, the electrochemical test strip can include means for determining the temperature of the sample. This can be, for example a liquid crystal strip, such one supplied by Temperature Technology, Inc. of Adelaide, South Australia, which is described at www.t-tec.com.au/2003/thermistors/LiquidC.html/. Alternatively, the means for determining the temperature of the sample can be part of the meter, such that it is reused, rather than part of a disposable strip. When the temperature sensing device is part of the meter, large and more expensive components can be reasonably employed, for example thermistors, and thermocouples.

Further, electrochemical test strips useful in the invention can include other additional features that are not necessary to the determination of oxygen carrying capacity as described herein, but which may be useful in determining analyte. For example, the electrochemical test strip may include one or more additional electrodes which can be reference electrodes, electrodes for determining sufficiency of sample volume, or electrodes for determining the time of sample application.

IV. Determination of Analyte, Such as Glucose

There are a variety of known methods for electrochemically determining analytes such as glucose in samples, and the present invention which includes an additive correction for oxygen attrition can be employed in the context of any of these methods. The following discussion is provided by way of non-limiting example.

Figure 2:
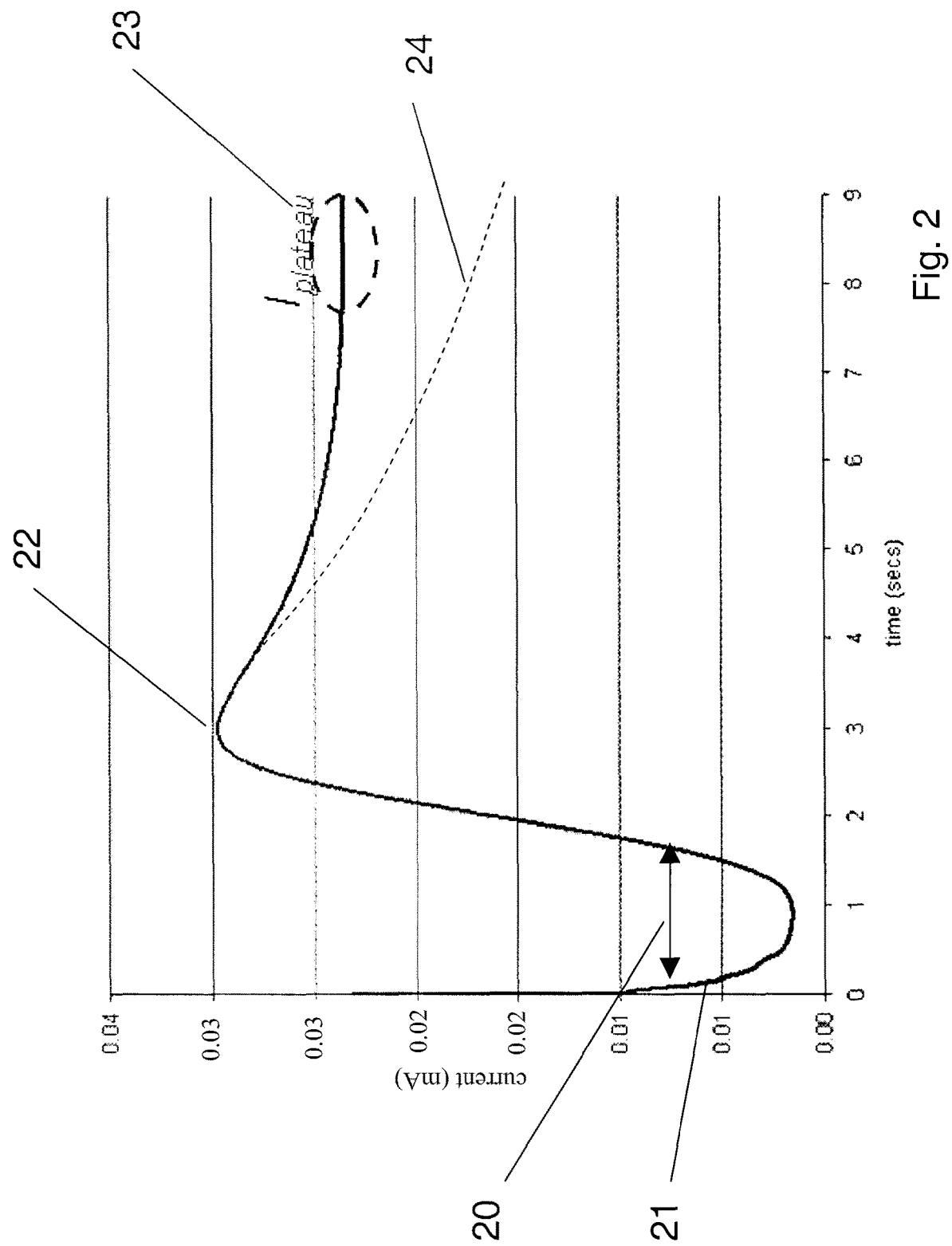
FIG. 2 shows current versus time profiles observed in two different electrochemical test strip configurations, one with facing electrodes and one with side-by-side electrodes.

FIG. 2 shows current versus time profiles observed in two different electrochemical test strip configurations, one with facing electrodes and one with side-by-side electrodes, where the electrochemical reagents are initially disposed only on the working electrode, and not on the counter electrode. In both cases, the current trace shows an immediate initial current 21 on the time scale shown following application of the potential. This current is associated with the initial charging of the double layer at the surface of the electrodes. Thereafter, the current decreases, because current is dependent on the mediator diffusing from the working electrode to the counter electrode. The duration of this reduced current (indicated by arrow 20) is dependent on the distance between the electrodes, and on the mobility of the mediator. After the period of reduced current 20, the current rapidly rises to a peak current 22. In the case of facing electrodes, the current declines to a plateau current 23 which reflects the recycling or shuttling of mediator between the electrodes. In the case of side-by-side electrodes, the current continues to decay in the time scale indicated, as indicated by dashed line 24. At longer times, this curve 24 also shows effects of recycling/shuttling of mediator.

In the region of the decay following the peak, before recycling becomes dominant, the current decay can be modeled by the Cottrell equation, i.e., $$1/I^2 \propto t$$

where I is the current and t is time. The square root of the slope of $1/I^2$ versus t is a parameter called the Cottrell slope. Cottrell analysis can be utilized to determine glucose concentration as described in U.S. Pat. Nos. 5,243,516; 5,352,351 and 6,284,125.

The present invention can also be used in combination with other electrochemical techniques that determine analyte concentration. For example, the analyte concentration can be detected using coulometric analysis, as described in U.S. Pat. No. 6,592,745, which is incorporated herein by reference; or using a conduction cell plateau current, as described in U.S. patent application Ser. No. 10/924,510, which is incorporated herein by reference.

V. Determination of Additive Correction Factor

The additive correction factor can be assessed by any technique that gives a measure of oxygen carrying capacity, in combination with a temperature measurement for the sample. The present inventors have found that a graph of measured raw analyte concentration versus a measure of oxygen carrying capacity is a line with a slope that is dependent on the temperature at which the measurements are made, but that is independent of $pO_2$ and glucose concentration over normal ranges of values. Changes in $pO_2$ or glucose concentration result in an additive offset of the graphed lines, but not a change in slope. (See FIGS. 5A and B) A plot of this slope as a function of temperature (See FIG. 5C) can be used to define slope (S) and intercept (I) parameters that are combined into the additive correction factor of the invention for a given temperature T, in accordance with the equation:

$$\text{additive correction factor} = \text{constant} \times [(S \times T) + I] \times OCC$$

where OCC is a measure of oxygen carrying capacity such as hematocrit, and the constant is an empirically determined factor with a positive or negative sign.

Accuracy of the additive correction factor can be improved when there is a large body of data gathered at one temperature and a limited body of data gathered at the measurement temperature by determining only the slope from the data gathered at the measurement temperature and determining the intercept from all of the available data. Thus, in the case where a large body of standard calibration data is available for the parameter I may be a constant established for the strip and meter combination, and only the slope need to be determined experimentally.

(a) Use of $t_{mob}$ as a measure of oxygen carrying capacity

In one embodiment of the invention, $t_{mob}$, a measure of the mobility of the mediator is used as the measure of oxygen carrying capacity.

Figure 3:
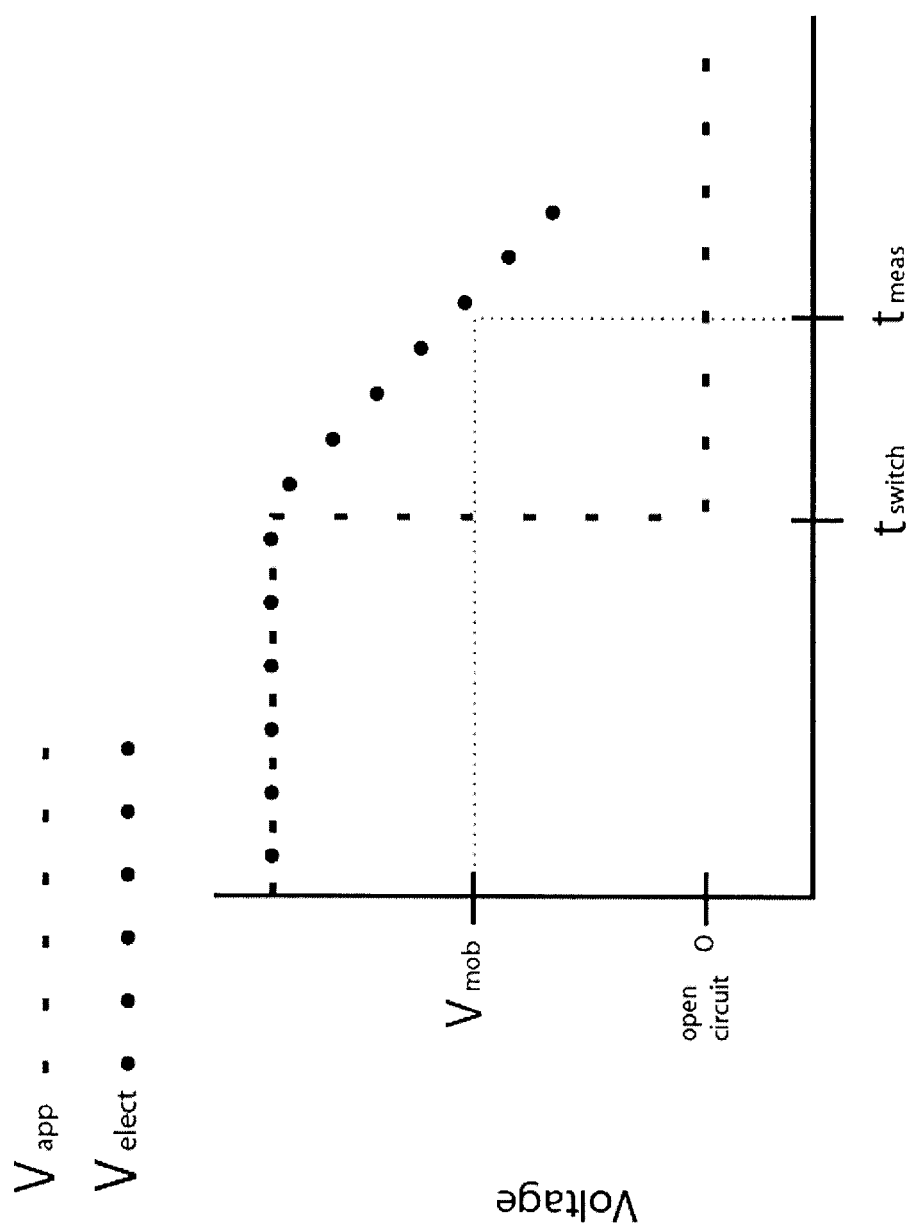
FIG. 3 shows a plot of voltage versus time, when applied voltage is switched off.

After measurements sufficient to allow determination of a raw analyte concentration, the applied potential is switched off at a time $t_{switch}$. At this point, a chemical potential gradient exists between the electrodes as a result of the unequal distribution of oxidized and reduced mediator. This chemical potential gradient decays over time after the potential is switched off, and the rate of this decay is dependent on the mobility of the mediator in the sample. (See commonly assigned U.S. patent application Ser. No. 10/924,510, which is incorporated herein by reference.) FIG. 3 shows the applied potential, $V_{app}$, and the measured potential at the electrodes, $V_{elect}$, as a function of time (in arbitrary units), commencing at a time after the current measurement that is used in the apparatus to determine raw analyte concentration. Note that the conversion of measured current to a measurement of raw analyte concentration need not be done prior to the switching off of the potential.

In accordance with one embodiment of the present invention, the decay in potential is monitored until the observed potential has decreased to a pre-determined value, $V_{mob}$. Decreases to around 50 mV are convenient where the applied voltage is on the order of 300 mV, although somewhat smaller values such as 47 mV or 48 mV may be found to provide optimum results in particular experimental configurations. In general, $V_{mob}$ is suitably 0.025 to 0.1V For example, in glucose determinations with a $V_{app}$ of 250 to 300 mV, $V_{mob}$ is suitably in the range of 25 to 100 mV, preferably 45 to 50 mV.

The time at which this drop has occurred is noted on FIG. 3 as $t_{meas}$ and $t_{mob}$ is given by:

$$t_{mob} = t_{meas} - t_{switch}.$$

Other ways of determining a measure of the rate of decay may also be employed. For example, an instantaneous slope of the decay of the potential can be determined, or the decrease in voltage over a predetermined time can be used. The meter may also select a particular time window and perform a linear regression on V versus log(t) or ln(t) to find $t_{mob}$ which is the time to a particular voltage. If the $V_{mob}$ does not fall within the selected window, a projection based on this linear fit can be used. The specific methodology is not critical, provided that the value of the measured decay is taken into account in determining the correction function.

(b) Use of Other Techniques as a Measure of Oxygen Carrying Capacity

U.S. Pat. Nos. 6,287,451 and 6,475,372 discussed above disclose electrochemical methods for determination of hematocrit in a disposable test strip. The hematocrit measurement is used in a multiplicative correction, as opposed to the additive correction of the present invention. The measurement can be used in both modes, however, just as $t_{mob}$ is used for both types of corrections as described above. This is because hematocrit is a measure of the red blood cells, and red blood cells have an oxygen carrying capacity.

In order to use any type of hematocrit measurement in present invention, a series of calibration measurements are taken to obtain data point pairs of uncorrected analyte concentration and hematocrit at each of a plurality of temperatures. At each temperature, the data points are fit to a linear model and the slope of the line is determined. As noted above, this slope is independent of glucose and $pO_2$ such that while these parameters need to be kept the same across experiments, the particular values are not significant. The resulting slope/temperature data point pairs are then fitted to a linear model, to determine the slope and intercept which is incorporated into an additive correction factor as described above.

In some cases, the linear model may be sufficient only for a narrow range of the data. An improved additive correction factor may be determined for a wider range of temperatures or oxygen carrying capacities by introducing non-linear terms such as quadratic equations of exponents to terms.

VI. Correction of Analyte Value

In the method of the invention, correction for the chemical effects of oxygen is done by adding an offset to the uncorrected analyte reading, to produce a corrected value. Additional corrections can be employed in combination with the additive correction of the invention. For example, multiplicative corrections relating to physical hematocrit effects, calibration corrections specific for individual lots of test strips, and corrections for other interferents may also be made. In addition, as is well known in the art, look-up tables or other conversion mechanisms can be used to convert determined signals into user-understandable values of analyte concentration in defined units.

VII. Dynamic Switching from Amperometric to Potentiometric Mode

In the present application, the meter first acts in an amperometric mode, and then after the applied potential is switched off, in a potentiometric mode. In order to enhance the quality and consistency of measurements made when operating in potentiometric mode, if is desirable to perform the switch to potentiometric mode only after a stable diffusion gradient of oxidized and reduced mediator has formed within the electrochemical test cell. In general, the potentiometry measurements will give the same stable reading at any point after the concentration gradients have formed a stable profile that extends "far enough" into the bulk of the sample.

To maximize the chances that stable diffusion gradients have been achieved, it is possible to simply establish a time after the start time of the measurement cycle at which the switch will be made. This time is determined empirically for a given test strip design, but may generally be on the order of 4 to 8 seconds. To allow the meter to accommodate a variety of different sample characteristics, however, $t_{switch}$ can be determined dynamically.

In one embodiment of the invention, $t_{switch}$ is determined dynamically from the determined value of $t_{peak}$ (the time of peak 22, in FIG. 2) by adding a time interval, for example 2 to 3 seconds to the determined value of $t_{peak}$.

In another embodiment of the invention, $t_{switch}$ is determined dynamically using a fixed value of $t_{switch}$ when $t_{peak}$ is small and $t_{peak}$ plus a predetermined amount when $t_{peak}$ is larger. For example $t_{switch}$ may have a fixed value of 3.5 second when $t_{peak}$ is less than 1.5 seconds, and be equal to $t_{peak}$ plus an offset (for example 2 second) when $t_{peak}$ is greater than 1.5 seconds.

In yet another embodiment, a third mode for measurement is established for circumstances when $t_{peak}$ occurs at times that are longer than ordinary. In this case, when $t_{peak}$ occurs above a predetermined threshold, for example 5 seconds, $t_{switch}$ is suitably determined as a function of $t_{peak}$ and an additive correction factor that uses predetermined constants derived from the slope of the Cottrell current.

Further, a maximum value of $t_{peak}$ can be established above which an error message is generated.

VIII. Apparatus of the Invention

The method of the invention can be used with any strip as described above, provided that a meter apparatus is providing that can receive the strip and provide the necessary applications of voltage and signal processing. Such a meter also forms an aspect of the present invention. Thus, the invention provides a meter for receiving an electrochemical test strip having electrodes and providing a determination of an analyte in a sample applied to the electrochemical test strip when received in the meter, said meter comprising (a) a housing having a slot for receiving an electrochemical test strip;

(b) communications means for receiving input from and communicating a result to a user; and (c) means for determining a raw analyte concentration value, and for determining an additive correction factor for the amount of oxygen in the sample, and modifying the raw analyte concentration to provide a corrected determination of analyte in the sample, wherein the additive correction factor for the amount of oxygen in the sample is determined as a function of the temperature of the sample and a measurement that reflects the oxygen carrying capacity of the sample.

Figure 6:
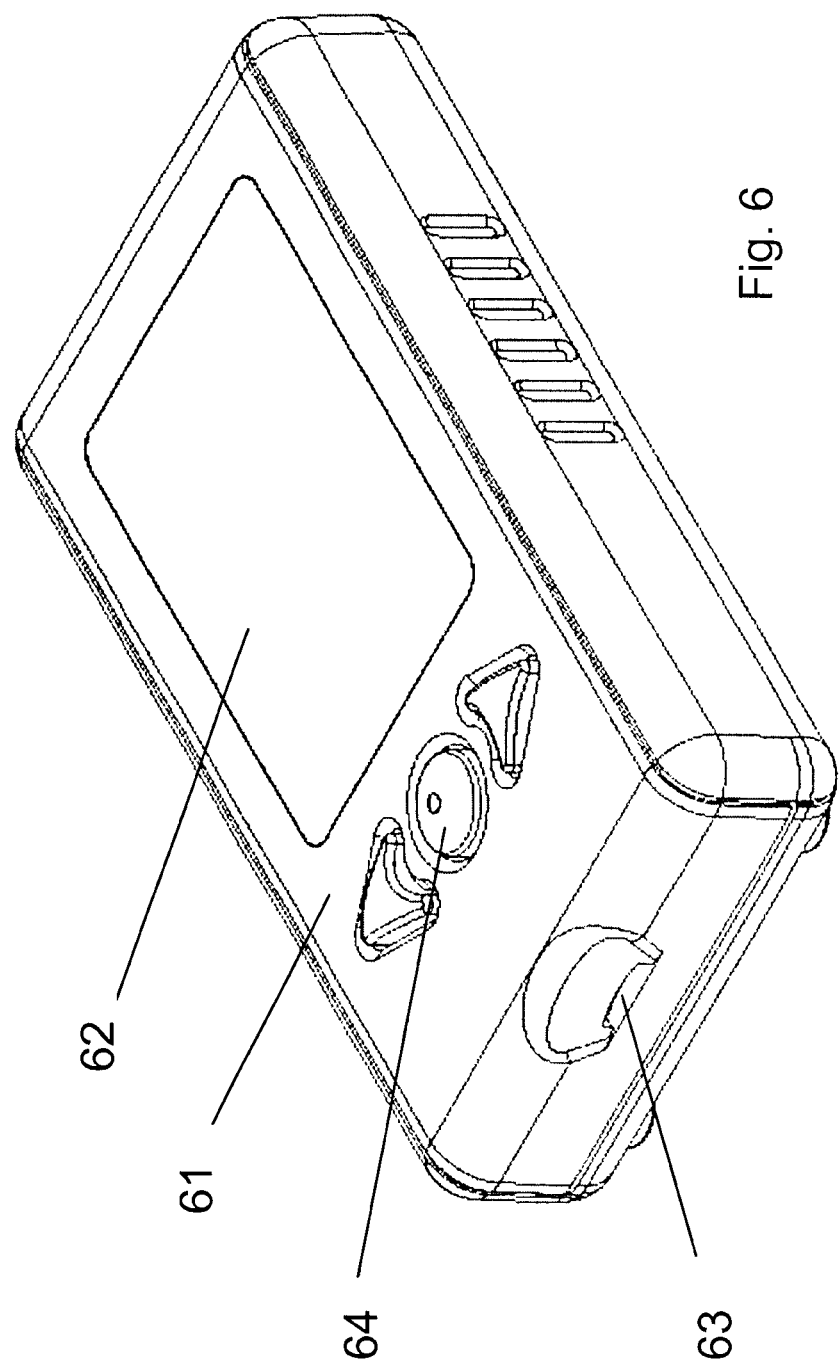
FIG. 6 shows an exterior view of a meter.

When not present in the strip, the meter of the invention also includes a means for measuring the temperature of the sample in the meter, for example a thermistor or thermocouple. FIG. 6 shows an external view of a meter in accordance with the invention. The meter has a housing 61, and a display 62. The housing 61 has a slot 63, into which a test strip is inserted for use. The meter may also have a button 64 for signaling the start of the measurement cycle, or may have an internal mechanism for detecting the insertion of a test strip or the application of a sample. Such mechanisms are known in the art, for example from U.S. Pat. Nos. 5,266,179; 5,320,732; 5,438,271 and 6,616,819, which are incorporated herein by reference. In the meter of the invention, buttons, displays such as LCD displays, RF, infrared or other wireless transmitters, wire connectors such as USB, parallel or serial connections constitute means for receiving input from and communicating a result to a user, and can be used individually and in various combinations.

Figure 7:
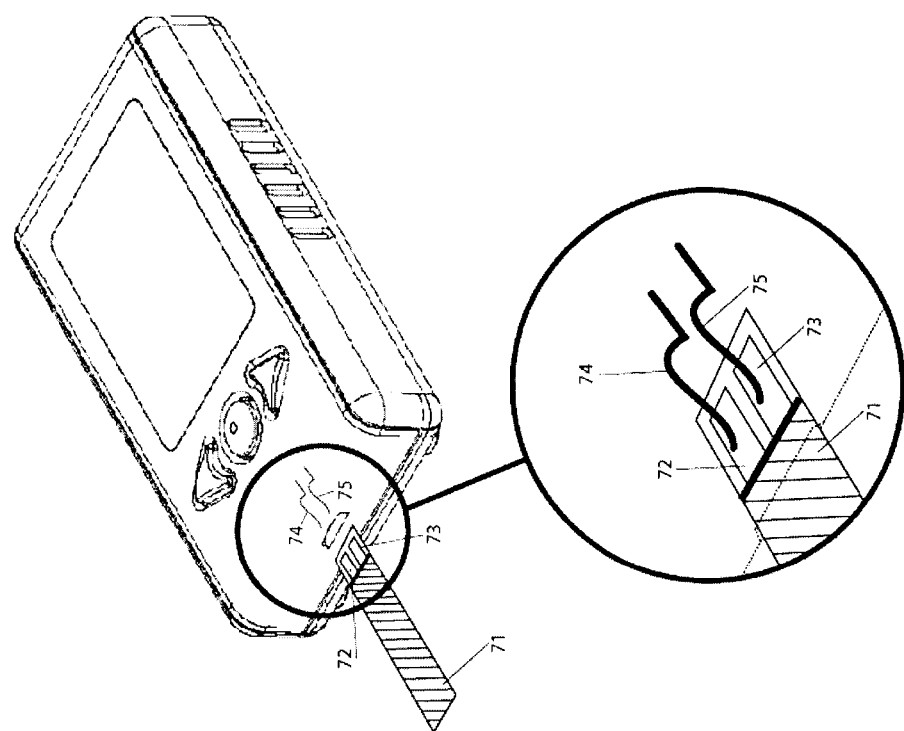
FIG. 7 shows connection of a test strip and connectors in a meter.

FIG. 7 shows an interior view in which the connection of the meter to a test strip is shown. As shown, the test strip 71 has contacts 72, 73 by which the electrodes are placed in electrical contact with contacts 74, 75 of the meter.

The means for determining a raw analyte concentration value, and for determining an additive correction factor for the amount of oxygen in the sample, and modifying the raw analyte concentration to provide a corrected determination of analyte in the sample comprises circuits, such as on a circuit board, associated with a programmed microprocessor that interacts with the circuits to provide the desired switching between amperometric and potentiometric modes and to monitor current and voltage as described. Apparatus suitable for switching between an amperometric mode of operation in which current is measured and a potentiometric mode of operation in which a potential difference between the electrodes is measured are described in commonly assigned US Provisional Applications Nos. 60/521,592, filed May 30, 2004, and 60/594,285 filed Mar. 25, 2005, and commonly assigned U.S. patent application Ser. No. 10/907,790, filed Apr. 15, 2005, which are incorporated herein by reference.

Figure 8:
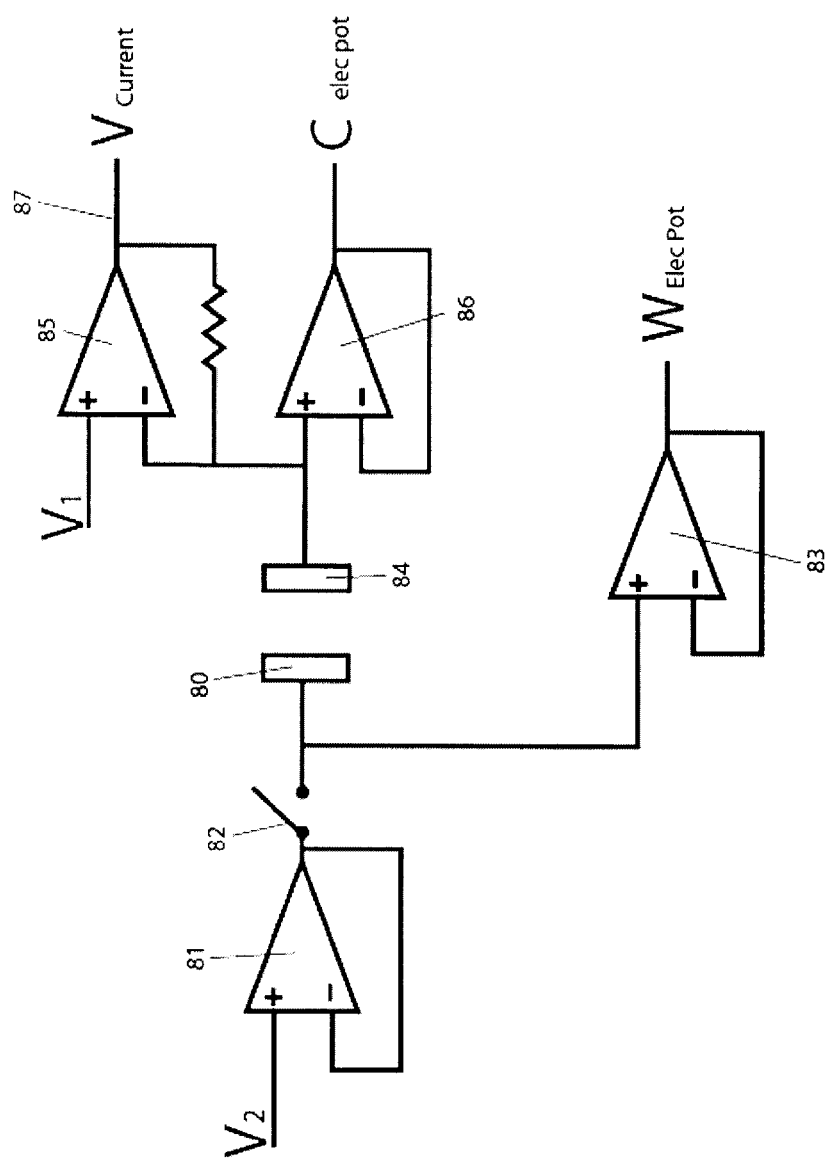
FIG. 8 shows a circuit diagram for switching between amperometric and potentiometric modes.

FIG. 8 shows an electrical schematic of the amperometric/potentiometric portion of one embodiment of the meter of the invention. It will be appreciated, however, that other components can also be used, which achieve the same results in terms of applying and switching the voltage. Working electrode 80 is connected to op amp 81 via a connector containing switch 82, and to op amp 83. Counter electrode 84 is connected to op amps 85 and 86. Op amps 83, 85 and 86 are high impedance input amplifiers. When operating in amperometric mode to determine an analyte, a voltage $V_2$ is applied to op amp 81, and a voltage $V_1$ is applied to op amp 85, $V_2$ being greater than $V_1$. The resulting potential difference between the electrodes results in the generation of a current that is related to the amount of analyte, and this current can be monitored at output 87 and converted to an indication of the presence or amount of analyte. When switch 82 is opened to create an open circuit and stop application of the potential difference, current flow ceases, and the output of amplifier 86 assumes the potential of the counter electrode, while the output of amplifier 83 assumes the potential of the working electrode 80. The difference between the output from op amp 83 and op amp 86 indicates the decay in chemical potential and is processed in accordance with the methods described above to determine the mobility of the mediator.

Figure 9:
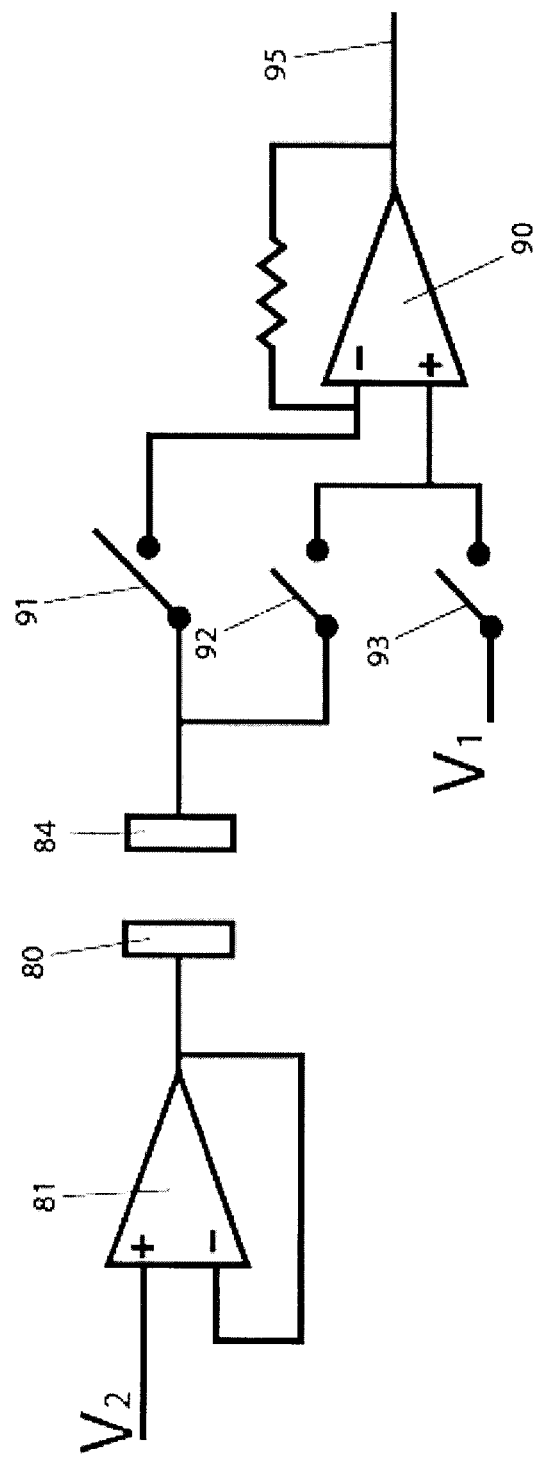
FIG. 9 shows a circuit diagram for switching between amperometric and potentiometric modes.

FIG. 9 shows an alternative version of this circuit using only two op amps and an increased number of switches. Working electrode 80 is connected to op amp 81 which receives input voltage $V_2$. Counter electrode 84 is connected to high input impedance op amp 90 via one of two switched paths. Input voltage $V_1$ is connected to the circuit via a third switched path. When switch 91 and 93 are closed, and switch 92 is open, the circuit functions in amperometric mode, and the output at 95 reflects current flow at the electrodes. When switch 92 is closed, and switches 91 and 93 are open, the circuit operates in potentiometric mode and the output at 95 assumes the potential of the counter electrode (similar to amplifier 86 in FIG. 8). Thus, the output at 95 indirectly reflects the difference in potential between the electrodes. The actual difference in potential between the electrodes is the difference between the output at 95, and the output of op amp 81 (at 80, the working electrode).

In one embodiment of the invention, the apparatus fits stored data points (t,V) extending from $t_{switch}$ to a time after the expected time $t_{meas}$ to the model equation $V(t)=a_1 \times \ln(t)+a_2$ by a least squares regression. The resulting values of $a_1$ and $a_2$ are then used to calculate the value of $t_{meas}$ at which the potential has fallen to $V_{mob}$ according to the equation $$t_{meas} = e^{\left(\frac{V_{mob}-a_1}{a_2}\right)}$$

The apparatus retrieves stored values for the slope and intercept of the raw concentration/temperature plot and the constant, determined from calibration runs using the same meter and test strip configuration and combines these values with the determined $t_{mob}$ to calculate the correction factor according to the equation:

additive correction factor=constant×[(S×T)+I]×$t_{mob}$

This additive correction factor is then added to the raw analyte concentration.

IX. Measurement System

In actual use, the meter described above is combined with an electrochemical test strip for the determination of a particular analyte, such as glucose. This combination, referred to as a measurement system, forms a further aspect of the present invention.

X. Determination of Hematocrit

While the invention has been defined to this point in terms of making a correction in the measurement of an analyte, the disclosed determination of $t_{mob}$ can also be used independently, with or without a contemporaneous determination of an analyte, to assess the hematocrit of a blood sample. Thus, in accordance with a further aspect of the present invention a method is provided for determining hematocrit comprising the steps of:

(a) introducing a blood sample between first and second electrodes in an electrochemical test cell containing a redox active species that serves as a charge carrier;

(b) applying a potential for period for time sufficient to establish a chemical potential gradient between the electrodes, (c) switching off the applied potential at a time $t_{switch}$, and obtaining a value indicative of the rate of decay of the chemical potential gradient in the absence of applied potential, and (d) comparing the determined value of the rate of decay with a standard curve relating rate of decay to hematocrit at the determined temperature to arrive at a value for the hematocrit of the sample. One suitable measure of the rate of decay is $t_{mob}$ as described above. A more refined measure of hematocrit may be obtained by also determining the temperature and using a value like the additive correction factor described above for comparison.

The redox active species in this aspect of the invention can be a mediator, which interacts with glucose and glucose oxidase as described above, or with some other redox active species that is inherently present in blood. Particularly where no determination of analyte is being made, however, the redox-active species may also be an added material, such as a mixture of ferricyanide and ferrocyanide ions, which can give current at the positive electrode by oxidation of ferrocyanide and at the negative electrode by reduction of ferricyanide at the applied potential.

The apparatus for measuring hematocrit differs from the meter in three significant respects. First, the programming for determining an analyte and displaying the results are optional. Second, the programming includes a look up table or other conversion mechanism for taking the measured value of the rate of decay and optionally the temperature and converting it into a value for hematocrit in conventional units. Third, the programming provides for display of the hematocrit value.

XI. Distinguishing Samples from Control Solutions

Some known analyte test meters have included the ability to automatically distinguish between strips to which a blood sample is applied and strips to which a control solution (for example analyte solution in water, viscosity-adjusted analyte solutions, or plasma containing a known amount of analyte) is applied. (See for example U.S. Pat. Nos. 6,645,368 and 6,824,670). The measurement of $t_{mob}$ as described herein, with or without consideration of temperature can also be used for this purpose.

Thus, in accordance with a further embodiment of the invention, a method and apparatus are provided in which material is applied to the test strip disposed in the apparatus, the material is identified as a blood sample or a control solution, and the signal from the test strip is processed as test sample or a calibration run based on this identification, wherein, the identification of the material as a sample or control solution is performed by the steps of:

(a) applying a potential for a period of time sufficient to establish a chemical potential gradient between the electrodes, (b) switching off the applied potential at a time $t_{switch}$, and obtaining a value indicative of the rate of decay of the chemical potential gradient in the absence of applied potential, and (c) comparing the determined value of the rate of decay with a threshold value, wherein a value on one side of the threshold value indicates that the material is a blood sample, and a value on the other side of the threshold value indicates that the material is a control solution.

In one embodiment of this aspect invention, the square root of the determined $t_{mob}$ is compared to a threshold value. The specific numerical threshold value will depend on the meter and the strip, and can be determined by testing a plurality of blood samples and control solutions and determining the threshold value that distinguishes between the two data sets with the desired degree of confidence. For example, a longer time measurement $t_{mob}$ or a slower rate than the threshold value is indicative of a blood sample.

This measurement of hematocrit can also be used to provide patient/user with an indication of anemia or other abnormal levels of red blood cells. In such an embodiment, a medically appropriate definition of anemia is used to define a threshold. The processor is set to compare the determined hematocrit value with this threshold, and provide an indication of anemia or normal red blood cell count based on the result of the comparison. If desired, intermediate thresholds can be used to establish degrees of red blood cell deficiency for better characterization of borderline cases. Since the same measurements are being used that are used for analyte determination, measurements of hematocrit, or anemia warning indications can be provided in a meter dedicated for this purpose, or in a combination meter that also tests for an analyte such as glucose.

XII. Examples

The invention will now be further described with reference to the following non-limiting examples. In these examples, measurements were made using electrochemical test strips having facing screen printed carbon electrodes, a nominal sample volume of 625 nanoliters, and a viewing window. Blood samples used in the tests were freshly drawn (less than 8 hours old) using Vacutainer™ tubes, and were stabilized with EDTA as an anticoagulant. Blood samples with various hematocrits were prepared by centrifuging a blood sample of known hematocrit of 40 and known glucose concentration, removing enough plasma to leave a hct 60 sample, and then creating a lower hematocrit of 20 by mixing equal volumes plasma and hct 40 blood. Because these samples were all prepared rapidly from a single blood sample, they all have the same plasma glucose concentration. Different glucose concentrations were generated by adding amounts of 1M glucose stock solution to blood prior to centrifugation.

After application of the blood sample, 300 mV was applied to the strips following a profile as shown in FIG. 3. $t_{mob}$ was determined based on a $V_{mob}$ of 47 mV. The slope in the Cottrell region of the current versus time plot (see FIG. 2) was determined and an "uncorrected" value for glucose concentration (as inferred from the actually measured mediator concentration) was determined in the meter as $$\sqrt{\frac{t_{mob}}{Cottrellslope}}$$

This value already includes a mobility-type physical correction.

In referring to the measured quantity as an uncorrected or raw glucose concentration, it should be understood that what was actually measured in this instance was reduced mediator (the charge carrier at the electrodes), and that this measurement is converted (using a look up table and/or calibration values in the meter) to a glucose value.

Figure 5A:
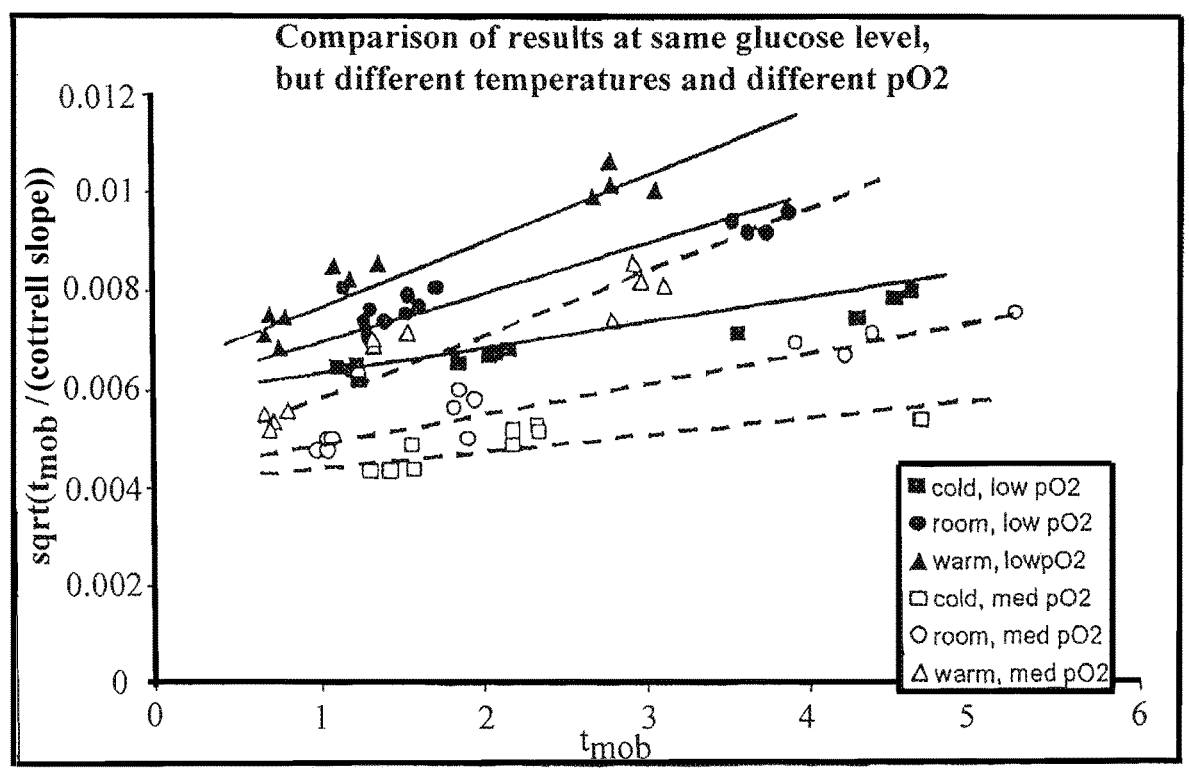
FIGS. 5A and 5B show the relationship between a measured indication of analyte concentration and tmob under various conditions of temperature, $pO_2$ and glucose concentration.

FIG. 5A shows results obtained at a single glucose level and two different values for $pO_2$ when samples were run at three different temperatures. While each of the lines in the graph is different, the important observation for purposes of this invention is that at any given temperature, the lines for different $pO_2$ values have the same slope. They are simply offset. For example, line 501 which is the cold temperature, low $pO_2$ line has the same slope as line 502, the cold temperature, medium $pO_2$ line.

Figure 5B:
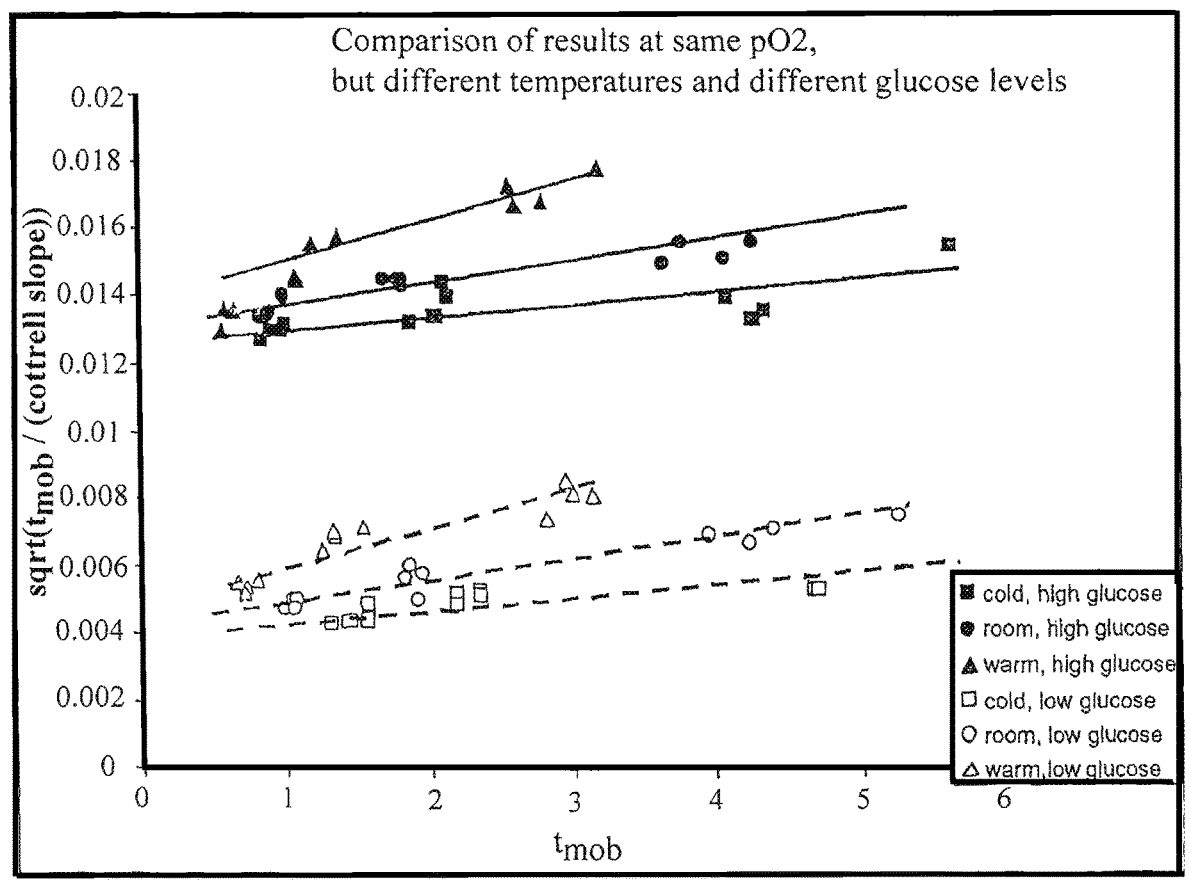

FIG. 5B shows similar results obtained at a single $pO_2$ level and two different values for glucose (~3.5 mM and ~9 mM) when samples were run at three different temperatures. Again, while each of the lines in the graph is different, the important observation for purposes of this invention is that at any given temperature, the lines for different glucose values have the same slope. They are simply offset. For example, line 510 which is the cold temperature, high glucose line has the same slope as line 511, the cold temperature, low glucose line.

Figure 5C:
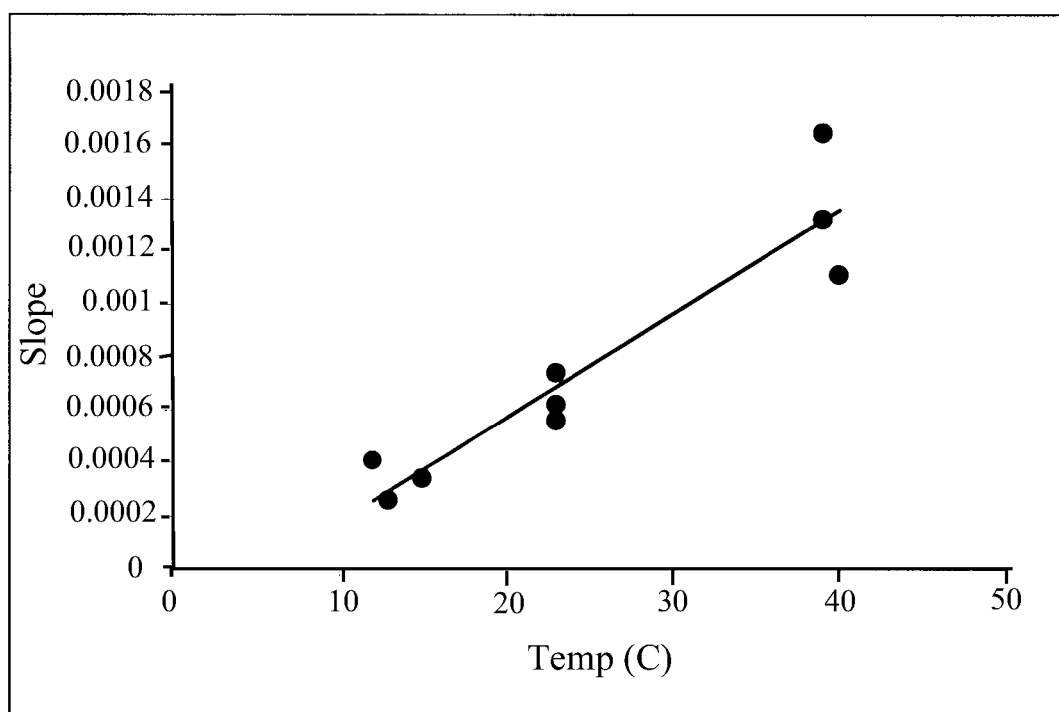
FIG. 5C shows a plot of the slope of the lines in FIGS. 5A and B as a function of temperature.

FIG. 5C shows a graph of the slope of each of these lines as a function of temperature, fit to a linear model. This plot was used to determine the slope and intercept values (S and I) for the meter and test strip combination employed. These values are used to generate the additive correction factor according to the formula:

additive correction factor=constant×[(S×T)+I]×$t_{mob}$

In the meter and strips employed for this testing, using the uncorrected analyte concentration as described above, the constant is −1.

Those skilled in the art will have no difficulty devising myriad obvious improvements and variations of the invention, none of which depart from the invention and all of which are intended to be encompassed within the scope of the claims which follow.

What is claimed is:

1. A method for determining an analyte in a sample comprising the steps of:
    (a) placing the sample in an electrochemical test cell comprising a working and a counter electrode and a mediator that serves as a charge carrier in the electrochemical determination of the analyte,
    (b) electrochemically determining an uncorrected result for the determination of analyte in the sample;
    (c) determining an additive correction term for the amount of oxygen in the sample, and
    (d) modifying the uncorrected result of step (b) by adding the additive correction term of step (c) to provide a corrected determination of analyte in the sample,
    wherein the additive correction term for the amount of oxygen in the sample is determined as a function of the temperature of the sample and a measurement that reflects the oxygen carrying capacity of the sample, and
    wherein the measurement that reflects the oxygen carrying capacity of the sample is determined by applying a potential for a period of time sufficient to establish a chemical potential gradient between the electrodes, switching off the applied potential at a time $t_{switch}$, and obtaining a value indicative of the rate of decay of the chemical potential gradient in the absence of applied potential.

2. The method of claim 1, wherein the sample is a blood sample.

3. The method of claim 1, wherein the value indicative of the rate of decay is a time $t_{mob}$, which is determined by determining the time, $t_{meas}$, required for the potential to decay to a pre-determined voltage $V_{mob}$, and wherein $t_{mob}=t_{meas}-t_{switch}$.

4. The method according to claim 3, wherein the predetermined voltage is from 25 to 100 mV.

5. The method according to claim 3, wherein the predetermined voltage is from 45 to 50 mV.

6. A meter for receiving an electrochemical test strip having electrodes and providing a determination of an analyte in a sample applied to the electrochemical test strip when received in the meter, said meter comprising
    (a) a housing having a slot for receiving an electrochemical test strip;
    (b) communications means for receiving input from and communicating a result to a user; and
    (c) a programmed microprocessor comprising instructions for:
    (i) determining an uncorrected result for the determination of analyte in the sample, determining an additive correction term for the amount of oxygen in the sample,
    (ii) modifying the uncorrected result by adding the additive correction term of step (c) to provide a corrected determination of analyte in the sample,
    (iii) determining the additive correction term for the amount of oxygen in the sample as a function of the temperature of the sample and a measurement that reflects the oxygen carrying capacity of the sample, and
    (iv) determining the measurement that reflects the oxygen carrying capacity of the sample by applying a potential for a period of time sufficient to establish a chemical potential gradient between the electrodes, switching off the applied potential at a time $t_{switch}$, and obtaining a value indicative of the rate of decay of the chemical potential gradient in the absence of applied potential.

7. The apparatus of claim 6, wherein the sample is a blood sample.

8. The apparatus of claim 6, wherein the instructions indicate that the value indicative of the rate of decay is a time $t_{mob}$, which is determined by determining the time, $t_{meas}$, required for the potential to decay to a pre-determined voltage $V_{mob}$, and wherein $t_{mob}=t_{meas}-t_{switch}$.

9. The apparatus according to claim 8, wherein the instructions indicate that the predetermined voltage is from 25 to 100 mV.

10. The apparatus according to claim 8, wherein the instructions indicate that the predetermined voltage is from 45 to 50 mV.

11. The apparatus of claim 8, wherein the instructions fit stored data points (t,V) extending from $t_{switch}$ to a time after the expected time $t_{meas}$ to the model equation $V(t)=a_1 \times \ln(t)+a_2$ by a least squares regression, and wherein the resulting values of $a_1$ and $a_2$ are used to calculate the value of $t_{meas}$ at which the potential has fallen to $V_{mob}$ according to the equation $$t_{meas} = e^{\left(\frac{V_{mob}-a_1}{a_2}\right)}.$$

12. The apparatus according to claim 6, further comprising means for determining the temperature of the sample.

13. A measurement system comprising a meter in accordance with claim 6, and an electrochemical test strip disposed within the housing.

14. The measurement system of claim 13, wherein the electrochemical test strip measures glucose in a sample.

* * * * *